United States Patent [19]

Wilbur et al.

[11] Patent Number: 5,045,303

[45] Date of Patent: Sep. 3, 1991

[54] RADIOHALOGENATED SMALL MOLECULES FOR PROTEIN LABELING

[75] Inventors: Daniel S. Wilbur; Alan R. Fritzberg, both of Edmonds, Wash.

[73] Assignee: NeoRx Corporation, Seattle, Wash.

[21] Appl. No.: 137,952

[22] Filed: Nov. 23, 1987

Related U.S. Application Data

[63] Continuation of Ser. No. 735,392, May 17, 1985, abandoned.

[51] Int. Cl.[5] ...................... A61K 49/02; A61K 49/00

[52] U.S. Cl. ...................................... 424/1.1; 548/542; 558/390; 564/183

[58] Field of Search ......................... 548/542; 424/1.1; 558/390; 564/183

[56] References Cited

U.S. PATENT DOCUMENTS

| | | | |
|---|---|---|---|
| 3,979,506 | 9/1976 | Smith . | |
| 4,115,374 | 9/1978 | Ryan et al. | 530/331 X |
| 4,279,887 | 7/1981 | Baldwin et al. | 424/1.1 X |
| 4,284,619 | 8/1981 | Lin | 424/1.1 |
| 4,450,149 | 5/1984 | Kabalka . | |
| 4,473,544 | 9/1984 | Machulla et al. | 424/1.1 |

OTHER PUBLICATIONS

Z. V. Svitra et al., "Synthesis and Reactions of p--Trimethylsilylphenylpropionic Acid", Seventh Rocky Mountain Regional ACS Meeting, Albuquerque, N.M., Jun. 6-8, 1984.

D. S. Wilbur et al., "Radiolabeled Phenylalkanoic Acids for Protein Labeling. Investigation of Arylsilanes as Intermediates for Radiolabeled Phenylpropionic Acids and Acid Derivatives", International Chemical Congress of Pacific Basin Societies, Honolulu, Hi., Dec. 16-21, 1984.

Blau et al., "p-Iodobenzoyl Groups as a Paired Label for In Vitro Protein Distribution Studies: Specific Localization of Anti-Tissue Antibodies", *International Journal of Applied Radiation and Isotopies* 3:217-225, 1958.

Wilbur and Svitra, "Electrophilic Radiobrominations of Hippuric Acid: An Example of the Utility of Aryltrimethylsilane Intermediates", *Journal of Labelled Compounds and Radiopharmaceuticals* vol. XXI, No. 5, pp. 415-428, 1984.

Riley and Perham, "The Reaction of Protein Amino Groups with Methyl 5-Iodopyridine-2-Carboximidate", *Biochem. J.* 131:625-635, 1973.

Coleman et al., "Aromatic Radiobromination Without Added Carrier", *J. Chem. Soc., Chem. Commun.* 1982, pp. 1276-1277.

Visser et al., "The Preparation of Aromatic Astatine Compounds Through Aromatic Mercury-Compounds", *Journal of labelled Compounds and Radiopharmaceuticals,* vol. XVII, No. 5, pp. 657-665, 1980.

Gilliland et al., "Iodine Labelled Radiopharmaceuticals from Arylthallium Bis(trifluoroacetate) Intermediates", *Journal of Radioanalytical Chemistry* 65:107-113, 1981.

M. Kosugi et al., "Palladium Catalyzed Reaction of Hexabutylditin with Aryl Bromides: Preparation of Negatively Substituted Aryltributyltin", *Chemistry Letters,* pp. 829-830, The Chemical Society of Japan, 1981.

Parham and Jones, "Elaboration of Bromoarylinitriles", *J. Org. Chem. 41:1187-1191, 1976.*

Wursthorn and Kuivila, "Synthesis of Substituted Aryltrimethylstannanes by the Reaction of Trimethylstannylsodium with Aryl Bromides", *Journal of Organometallic Chemistry* 140:29-39, 1977.

*Primary Examiner*—John S. Maples

[57] ABSTRACT

Haloaryl compounds are lithiated and thereafter metalated with one of the following organometallic groups: $Sn(n\text{-}Bu)_3$ or $SnMe_3$. The resulting aryltin compound can be transmetalated in site-specific reaction with one of the following organometallic groups: HgX, $Hg(OAc)_2$, $BX_3$, or $BZ_2$, wherein X is Cl, Br, or I, and Z is alkyl or alkoxy. The metalated compounds are subsequently radiohalogenated via a demetalation reaction. A functional group suitable for conjugation to protein can be added subsequent of preferably prior to the radiohalogenation.

Also compounds of the formula: $R_1$-Ar-$R_2$, wherein $R_1$ is either a radiohalogen or any one of the organometallic groups stated above, Ar is aromatic or heteroaromatic ring, and $R_2$ is a short-chain substituent that does not activate the aromatic ring and that bears a functional group, or a precursor thereof, suitable for conjugation to protein under conditions that preserve the biological activity of the protein.

The radiohalogenated small molecules are conjugated to proteins such as monoclonal antibodies for use in diagnosis and therapy.

7 Claims, No Drawings

RADIOHALOGENATED SMALL MOLECULES FOR PROTEIN LABELING

This is a continuation of the prior application Ser. No. 735,392, filed May 17, 1985, now abandoned, the benefit of the filing date of which hereby claimed under 35 USC 120.

TECHNICAL FIELD

This invention relates to radiohalogenated small molecules for labeling proteins, particularly antibodies, useful for clinical diagnosis and therapy, and to methods of introducing high specific activity radiohalogens into protein molecules.

BACKGROUND OF THE INVENTION

Radiohalogenated proteins have been the object of extensive scientific study and promise to be useful for a variety of clinical applications, both in vitro and in vivo. For example, radioiodinated ferritin is used in an in vitro diagnostic determination of ferritin concentration in serum. Radioiodinated thyroid stimulating hormone is employed in a similar assay.

Radionuclides of halogens possess properties that make them very attractive for both diagnostic imaging and radiotherapy. For example, radioiodine as iodine-123 ($T\frac{1}{2}=13$ h, 159 keV gamma, electron capture) is nearly ideal for imaging with the current gamma cameras, and iodine-131 ($T\frac{1}{2}=8$ d, 364 keV gamma, beta particle), while producing images of lower quality, has been demonstrated to be useful in clinical radiotherapy of the thyroid. Similarly, bromine radionuclides such as bromine-75 ($T\frac{1}{2}=1.6$ h, positron) and bromine-76 ($T\frac{1}{2}=16$ h, positron) have properties that make them attractive for positron tomographic imaging, and bromine-77 ($T\frac{1}{2}=2.4$ d, several gammas, electron capture) has properties that make it attractive for radiotherapy. Other radiohalogens, such as fluorine-18 ($T\frac{1}{2}=110$ min, positron) and astatine-211 ($T\frac{1}{2}=7.2$ h, alpha particle), are also attractive candidates for radioimaging and radiotherapy.

The development of monoclonal antibodies which localize in cancerous tissue due to their high specificity and affinity for antigens on tumor cell surfaces has increased the prospect of clinical applications of radiolabeled antibodies for diagnosis and/or therapy. The high specificity of the antibodies make them desirable candidates as carrier molecules to attach specific radionuclides for delivering radioactivity to a cancer site.

Unfortunately, there are presently no routine clinical dianostic or therapeutic applications of radiohalogen labeled antibodies for use in vivo. Direct radiohalogen labeling of antibodies and other proteins has proved to be difficult. Antibodies exhibit varying sensitivities to radiolabeling reaction conditions, and the oxidizing reaction conditions necessary for radiohalogenations are particularly deleterious. Direct radioiodination of proteins has become routine, but very often a measurable reduction of biological activity of the protein results. The stability of the attached radiolabel can also vary. For example, the loss of radioiodine from antibodies has been found to be as high as 50% in 24 hours for some labeled antibodies. Radiobrominations require even stronger oxidizing reaction conditions than radioiodinations, and attempts to radiobrominate proteins directly have met with little success unless expensive and difficult to obtain enzymes are used as oxidants.

Furthermore, direct radiohalogenation of proteins occurs primarily at tyrosyl residues, and the activated phenol ring of tyrosine contributes to an inherent electronic instability of the resultant ortho-substituted radiohalogen label. The radiohalogen label is also subject to steric hindrance effects and may in addition be available to deiodinase enzymes which catabolize the structurally similar thyroid hormones, e.g., thyroxine.

One approach that circumvents subjecting proteins to the harsh reaction conditions necessary for direct radiohalogenations is the use of small molecules that can be radiolabeled in a separate reaction vessel and subsequently coupled to proteins under mild reaction conditions. This approach is the basis of the commercially available Bolton-Hunter reagent, N-succinimidyl-3-(4-hydroxyphenyl)-propionate. Moderate radiolabeling yields are thereby obtained with radioiodine (35-60% yields of labeled proteins), but the stability of the radioiodine label suffers from the same problems as described for the chemically similar radioiodinated tyrosyl residues. Similarly, the commercially available Wood's reagent, methyl-p-hydroxybenzimidate, can be radioiodinated prior to attachment to proteins. However, the radioiodinated product is also plagued with the inherent instability of the ortho-iodinated phenol. Even though these reagents do not yield as stable a radiolabel as desirable, they have been extensively used for radioiodination because little deactivation of the protein results from their use.

The phenolic ring is employed in both the Bolton-Hunter and Wood's reagents because an activated aromatic ring is required in order to introduce high specific activity radioiodine into these molecules. It would be very desirable to be able to introduce radiohalogens into small molecules containing an aromatic ring other than a phenol so that the radiolabel would be more stably attached; furthermore, if the hydroxyl were not present the radiolabel would be less subject to electronic and steric hindrance effects.

Recent reports in the literature describe the use of organometallic intermediates to introduce high specific activity radiohalogens into non-activated aromatic rings of simple organic molecules, but not into more complex organic molecules that can be attached to proteins without the aforementioned disadvantages.

SUMMARY OF THE INVENTION

This invention provides a rapid and efficient method of introducing high specific activity halogen radionuclides into non-activated aromatic rings of small molecules that can be conjugated to proteins under conditions that preserve the biological activity of the protein. Substitution of the radiohalogen onto a non-activated aromatic ring provides a radiolabel with greater stability than prior art substitutions onto activated aromatic rings such as phenols. Furthermore, the radiohalogen can be substituted in positions such as para or meta on an aromatic ring which do not contain a hydroxy functionality in order to render it less susceptible to attack by deiodinase enzymes.

Pursuant to this method, haloaryl compounds are lithiated and thereafter metalated with one of the following organometallic groups: $Sn(n\text{-}Bu)_3$ or $SnMe_3$. The resulting aryltin compound can be transmetalated in site-specific reaction with one of the following organometallic groups: HgX, $Hg(OAc)_2$, $BX_3$, or $BZ_2$, wherein X is Cl, Br, or I, and Z is alkyl or alkoxy. Th metalated compounds are subsequently radiohalogenated via a demetalation reaction. A functional group suitable for conjugation to protein can be added subsequent or preferably prior to the radiohalogenation.

Also provided are compounds of the formula: $R_1$-Ar-$R_2$, wherein $R_1$ is either a radiohalogen or any one of the organometallic groups stated above, Ar is aromatic or heteroaromatic ring, and $R_2$ is a short-chain substituent that does not highly activate the aromatic ring and that bears a functional group, or a precursor thereof, suitable for conjugation to protein under conditions that preserve the biological activity of the protein.

The radiohalogenated small molecules of this invention can be conjugated to proteins as monoclonal antibodies for use in diagnosis and therapy.

DESCRIPTION OF THE PREFERRED EMBODIMENTS

The present invention is directed to radiohalogenated small molecules of the formula I:

*X-Ar-R I wherein *X is a radiohalogen, Ar is aromatic or heteroaromatic ring, and R is a short-chain substitutent that does not highly activate ring Ar onto which radiohalogen *X is substituted and that bears a functional group suitable for conjugation to protein under mild, e.g., acylation, conditions that preserve the biological activity of the protein. The compounds of formula I can be coupled to proteins, such as monoclonal antibodies or plasma proteins, (or to carriers such as amino acid polymers which can in turn be coupled to proteins), to provide reagents for diagnostic and therapeutic applications.

As utilized herein, the symbol *X indicates any radioisotope of: iodine, particularly I-123, I-125, and I-131; bromine, particularly Br- 75, Br-76, and Br-77; fluorine, particularly F-18; and astatine particularly At-211. Preferred radiohalogens *X for diagnostic imaging purposes include I-131 and most preferably I-123 for imaging with gamma cameras; and for positron tomographic imaging: F-18, Br-75, and Br-76. For clinical radiotherapy, preferred radiohalogens *X include I-131, Br-77, and At-211. Preferred radiohalogens *X for in vitro radioimmunoassay purposes include I-125 and I-131. Pursuant to this invention the radiohalogen *X is preferably para- or meta-positioned on ring Ar relative to substituent R in order to render the radiohalogen less succeptible to catabolism by dehalogenase enzymes.

The symbol Ar indicates any aromatic or heteroaromatic ring. Preferred rings Ar include benzene, pyridine, furan, and thiophene, the latter three because of the enhanced water solubility they convey. The attachment of the radiohalogen to a carbon atom in an aromatic ring is preferred over attachment to an alkyl carbon atom due to the increased bond strength of the carbon-halogen bond in the aromatic ring. The nature of the aromatic ring is not critical and may be mono-, bi-, tri-, or higher number of rings, but the monocyclic ring is preferred based on increased water solubility. The aromatic rings may consist of all carbon atoms or may contain heteroatoms such as nitrogen, oxygen, or sulfur. Inclusion of heteroaromatic rings such as pyridines, furans, or thiophenes can assist in increasing water solubilities of the radio iodinated small molecule conjugates. Further substitution on the aromatic ring, exclusive of *X and R, with polar substituents such as a nitro, sulfonic acid, carboxylic acid, or dialkyl amino group can also be used to enhance water solubility.

Increased water solubility is desirable to give higher yields and less potential aggregation in the conjugation reaction with protein and to cause less perturbation of the lipophilicity of the antibody conjugate. Other substituents can be added to impart some control against enzymatic degradation.

The symbol R indicates any substituent that meets the following three requirements: First, the R substituent must not highly activate ring Ar toward electrophilic substitution. In other words, R cannot be linked to ring Ar by a linkage that increases the electron density of Ar on the order of the increase produced by a hydroxy or amino substitution. Second, R should be a short-chain substituent so that unconjugated or cleaved radiohalogenated molecules can be rapidly removed by the kidneys. Thus, R may contain an alkyl or other spacer chain between the aryl linkage and the functional group for protein conjugation, but such a spacer chain should preferably contain no more than 5, and most preferably no more than 3, straight-chain carbon atoms. Third, the R substituent should bear a functional group that is available for conjugation to protein under mild conjugation conditions, such as acylation or amidination, that preserve the biological activity of the protein. Thus, R should provide a functional group (termed Q herein), such as imide ester or imidate ester, for covalent attachment to corresponding functional groups (or conjugated attachment sites) on amino acid or carbohydrate residues of proteins, glycoproteins, or carrier molecules such as amino acid polymers that can in turn be conjugated to protein molecules.

Suitable functional groups Q for the above-stated purpose include phenolic esters (e.g., para-nitrophenol), imide esters (e.g., succinimide ester), imidate esters, anhydrides, acylsuccinimides, aldehydes, isothiocyanates, diazo, amines, hydrazines, alkyl halides, maleimides, and other groups that can be used to attach the molecule to a protein through a covalent bond. Also within the ambit of this invention are radiohalogenated small molecules of formula I wherein the R substituent bears a precursor of functional group Q. Suitable precursors include: carboxylic acid where Q is phenolic ester, imide ester, anhydride, acylsuccinimide, or maleimide; nitrile where Q imidate ester; alcohols where Q is aldehyde; halide where Q is isothiocyanate or hydrazine; and amine where Q is diazo.

Representative R substituents include alkyl acids, amido alkyl acid, nitrile, alkyl nitriles, amido alkyl nitrile, imide ester, alkyl imide esters, amido alkyl imide ester, imidate ester, alkyl/imidate esters, and amido alkyl imidate ester.

Representative radiohalogenated small molecules of this invention include the compounds of formulas II and III:

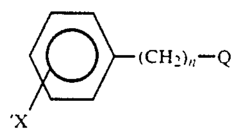

II

-continued

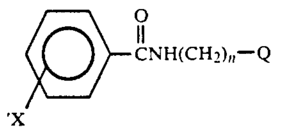

III wherein *X is radiohalogen as stated above, n is an integer, and Q is a functional group or a functional group precursor as stated above. The radiohalogen is preferably para- or meta-positioned on the aromtic ring in order to make the radiohalogen less susceptible to catabolism by deiodinase enzymes. The spacer component $(CH_2)_n$ can be a straight- or branched-chain alkyl or heteroalkyl group containing up to 12 but preferably no more than 5 straight-chain carbon atoms. In the most preferred embodiment no more than three straight-chain carbon atoms separate functional group Q from the aromatic ring; i.e., n=0,1,2or 3. In order to quickly clear background activity for diagnostic imaging, and ti minimize radiation dose to vital organs, the alkyl spacer component should be shortened so that non conjugated and chemically or enzymatically cleaved radiohalogenated compounds can be rapidly cleared through the kidnets, rather than via fatty acid degradation pathways in the hear or liver. On the other hand, for certain applications a short alkyl or heteroalkyl spacer between the radiolabeled aryl ring and the protein may be desirable.

Illustrative but nonlimiting examples of radiohalogenated small molecules of this inventin include: N-succinimidyl-3(4-[$^{131}$I]idophenyl)-propionate; methyl-3-(4-[$^{131}$I]idophenyl)propioimidate; N-succinimidyl-4-[$^{131}$I]iodobenzoate; methyl-4-[$^{131}$I]iodobenzimidate; N-succinimidyl-4-[$^{131}$I]iodobenzamidoacetate or N-succinimidyl-4-[$^{131}$I]iodohippurate; methyl-4-[$^{131}$I]iodobenzamidoacetimidate; and 4-[$^{131}$I]iodobenzamidoacetimidate; and 4-[$^{131}$I]iodobenzamidoacetonitrile.

Also provided by the present invention are organometallic intermediate molecules of formula IV:

M-Ar-R Iv wherein M is Sn(n-Bu)$_3$, Bu being butyl, SnMe$_3$,Me being methyl, HgX, X being Cl, Br. or I, HfOAc being acetate, B(OH)$_2$, or BZ$_2$, Z being alkyl or alkoxy, and both Ar and R are the same as defined with reference to formula I. Also within the ambit of this invention are organometallic intermediate molecules of formula IV wherein the R substituent bears a precursor, such as carboxylic acid or nitrile, of functional group Q. Organometallic group M is preferably para- or meta-positioned. Illustrative but nonlimiting examples of organometallic intermediate molecules of this invention include: N-succinimidyl-3-(4-tributylstannylphenyl)propionate; methyl-3-(4-tributylstannylphenyl)propiomidate; N-succinimidyl-4-tributylstannylbenzoate; methyl-4-tributylstannylbenzimidate; N-succinmidyl-4-tributylstannylbenzamidoacetate or N-succinimidyl-4-tributylstannylhippurate; methyl-4-tributylstannylbenzamidoacetimidate; and 4-tributylstannylbenzamidoacetonitrile.

A method is provided for synthesiaing the compounds of formula I. Briefly stated, a para- or meta-substituted haloaromatic derivative bearing a precursor to functional group Q is lithiated and thereafter metalated with one of the following organotin groups: Sn(n-Bu)$_3$ of SnMe$_3$. The resulting aryltin compound can be transmetalated in site-specific reaction with one of the following organomercury or organoboron groups: HgX, Hg(OAc)$_2$, BX$_3$, or BZ$_2$, wherein X is Br, I, or preferably Cl, and Z is alkyl or alkoxy. The stannylated or otherwise metalated compound is radiohalogenated via a demetalation reaction, preferably after functinal group Q is present.

Precursors of the organometallic intermediate molecules of formula IV are available through known chemistry or are commercially available. Suitable precursor molecules include: para-bromo and para-iodobenzoic acids (Pfaltz and Bauer, Stamford, Conn.); para-bromo and para-iodobenzonitriles (Pfaltz and Bauer). Synthesis of para-bromophenylpropionic acid in high yield is described below in Example 1. Conversion of the acid to the corresponding nitrile can be accomplished as described in *J. Org. Chem.* 41(7):1187-1191, 1976.

The stated organometallic groups are available through known chemistry and are commercially available, e.g., from Alpha Products, Danvers, M.A.

Syntheses of the subject organometallic intermediate compounds can be carried out be an initial metal-halogen exchange reaction of the corresponding halogenated precursor with n-butyl lithium at −100° C., followed by reaction of the lithio anion with a halide of one of the stated organotin groups, preferably tri-n-butyltin chloride. Transmetalation of the resulting aryltin compound with one of the stated organomercury or organoboron groups can then be made to achieve a site-specification substitution onto the aromatic ring. For example, transmetalation with BCl$_3$ yields the corresponding aryl BCl$_2$ compound, which can then be base converted to the corresponding aryl B(OH)$_2$ compound. Reaction with Hg(OAc)$_2$ yields the corresponding aryl HgOAc compound. Workup of the crude reaction mixture should be carried out at near neutral or basic conditions due to the acid instability of the aryltins in particular.

Attaching the yet-to-be radiolabeled compounds to proteins will require the availability of a functional group Q, such as can be provided by conversion of carboxylate precursor group into an ester containing a good leaving group, for example hydroxysuccinimide, or by conversion of cyano precursor into an imidate ester. Such conversions can be considered as activating the molecule towards reaction with a corresponding functional group, such as an amino group (e.g., lysine residues), or a thiol or hydroxy, on a protein. Due to the nucleophilic nature of the lithio intermediates, none of the activated imide and imadate esters or other above-stated functional groups Q can be synthesized before introducing the tri-n-butyltin functionality onto the aromatic ring. On the other hand, it is preferably to make the activated imide and imdate ester or other functional group Q prior to introducing the radiohalogen in order to avoid losses in radiochemical yields and the incorporation of radiochemical impurities that would otherwise result.

Conversion of the aryltin or otherwise metalated derivatives from free carboxylic acids to succinimidyl esters can be accomplished prior to the radiohalogenation step, using dicyclohexylcarbodiimide (DCC) and N-hydroxysuccinimide (NHS) in anhydrous tetrahydrofuran (THF). However, synthesis of imidate esters from cyano compounds is made problematical by the acid instability of the aryl-metal bond, particularly the aryltin bond. Thus, cyano containing compounds should be radiohalogenated prior to formation of the imidate ester. Such an esterification can be carried out in the same solvent as the radiohalogenation (e.g., MeOH) and can be accomplished within 30 minutes at 0°-5° C.

Radiohalogenation of the corresponding succinimidyl esters will yield the desired compounds via a site-specific demetalation reaction. Due to the possibility of hydrolysis of the succinimidyl esters, the reactions should be carried out using conditins that will minimize the reaction time. For example, the reactions can be brought to room temperature in order to minimize the hydrolysis by shortening the reaction time. As stated above, radiohalogenations of nitrile containing compounds should be made before converting the radiolabeled products to the corresponding imidate esters.

The radiohalogenation reaction mixture should have a dilute sodium thiosulfate solution added to it prior to any purification or workup procedure. Separation of any remaining radiohalide can then be easily accomplished on reverse-phase HPLC.

The radiohalogenation reactions are preferably carried out in $H_2O$ so that solvent need not be removed before reaction with protein. Protic solvents such as methanol or ethanol can also be used, in which case the solvent can be conveniently removed prior to addition of the radioactive compound to the protein solution (or vice versa). Alternatively, non-protic solvents (e.g., carbon tetrachloride) can be used for radiohalogenation since a biphasic system may provide a convenient method of separating free radiohalide from the labeled compounds.

The radiohalogenations can be monitored and purified by radio-HPLC, for example on a reverse-phase high performance liquid chromatography column (C-18) eluted with a mixture of MeOH/1% HOAc.

This invention is further illustrated by the following Examples.

EXAMPLE 1

Synthesis of para-bromophenylpropionic acid.

A flask containing 10.0 g 2,4,4-trimethyl-2-oxazoline (88 mmole) dissolved in anhydrous THF under nitrogen is allowed to equilibrate at −78° C. (dry ice/acetone bath) for 10 minutes. To this flask is slowly added 55 ml of n-butyl lithium (1.6N, 85 mmole). The light yellow solution is then transferred to a second flask containing 29.4 g (100 mmole) para-bromobenzylbromide in 200 ml anhydrous THF under nitrogen at −78° C. Once the addition is complete, the reaction mixture is stirred for 20 minutes at −78° C., then the cooling bath is removed and the stirring is continued for 3 hours.

A 200 ml volume of saturated $NH_4Cl$ is added (cautiously) and the two phases are separated. The THF layer is dried over anhydrous $MgSO_4$ and evaporated to yield an oil. This oil is dissolved in 200 ml dimethoxyethane and 100 ml 3N HCl, and is heated to reflux for 5 hours. The resultant solution is poured onto ice and the light tan solid is collected; (yield: about 17 g).

This solid is dissolved in approximately 300 ml 15% KOH and extracted with 200 ml diethylether. The KOH solution is diluted with ice and acidified with concentrated HCl. The white precipitate is collected and washed well with $H_2O$; (yield: about 10 g).

EXAMPLE 2

Synthesis of para-tri-n-butyltinbenzonitrile from para-bromobenzonitrile.

A flask containing 1 equivalent (e.g., 10 mmole) of para-bromobenzonitrile in freshly distilled anhydrous tetrahydrofuran is allowed to equilibrate at approximately −100° C. (diethyl ether/liquid nitrogen bath) for approximately 30 minutes under nitrogen. To the flask is then added 1.1 equivalents (e.g., 11 mmole) of a n-butyl lithium solution (2.3M in hexanes) at such a rate as to keep the reaction temperature below −90° C. After the addition is completed, the reaction mixture is stirred at approximately −100° C. for an additional five minutes.

Then a solution of 1.1 equivalents (e.g., 11 mmole) of tri-n-butyltin chloride in anhydrous tetrahydrofuran is added dropwise. As before, the addition is made at such a rate as to keep the reaction temperature below −90° C. After the addition is completed, the reaction mixture is stirred at −100° C. for 30 minutes. The cooling bath is then removed and the reaction mixture is allowed to come to room temperature.

The reaction mixture is then poured (carefully) into a beaker containing ice water saturated with ammonium sulfate. The tetrahydrofuran phase is separated and dried with anhydrous magnesium sulfate. Filtration of the magnesium sulfate and evaporation of the tetrahydrofuran under reduced pressure yields the corresponding para-tri-n-butyltinbenzonitrile compound.

EXAMPLE 3

Synthesis of para-tri-n-butyltinphenylpropionic acid is accomplished by reaction of para-bromophenylpropionic acid under the conditions described in Example 2, except that 2.2 equivalents (e.g., 22 mmole) of n-butyl lithium and 2.2 equivalents (e.g., 22 mmole) of tri-n-butyltin chloride are used in the reactions.

EXAMPLE 4

Synthesis of para-tri-n-butyltinhippuric acid is accomplished by reaction of para-bromohippuric acid as described in Example 2, except that 3.2 equivalents (e.g., 32 mmole) of n-butyl lithium and 3.2 equivalents (e.g., 32 mmole) of tri-n-butyltin chloride are used in the reaction.

EXAMPLE 5

Transmetalation reactions.

Mercuric acetate (4 mmole) is dissolved in 200 ml anhydrous THF at room temperature. The THF solution is cooled slightly (15°-20° C.) and a solution of any one of the above tributylphenyltin compounds (4 mmole) in 20 ml anhydrous THF is added in one portion. The resulting solution is stirred at room temperature for one hour and evaporated on a rotary evaporator at room temperature. The phenylmercuric acetate residue is dissolved in a minimum amount of THF (approximately 20 ml) and treated with aqueous KBr (10 mmole in 20 ml $H_2O$). The solution is then diluted with $H_2O$ (approximately 250 ml) and the precipitate is collected, washed with $H_2O$, washed with absolute ethanol, and dried under vacuum to give the corresponding phenylmercuric bromide.

Transmetalations involving organoboron groups are accomplished in like manner.

EXAMPLE 6

Syntheses of succinimide esters of para-tri-n-butyltinphenylpropionic acid and para-tri-n-butyltinhippuric acid.

A solution of 1.0 equivalents (e.g., 1 mmole) of the product of either Example 3 or Example 4 in anhydrous tetrahydrofuran is cooled to 0° C. (ice water bath). To the cooled solution is added 1.0 equivalents (e.g., 1 mmole) of N-hydroxysuccinimide, then 1.2 equivalents (e.g., 1.2 mmole) of dicyclohexylcarbodiimide. The reaction mixture is stirred at 0° C. for two hours and then placed in a refrigerator overnight. The precipitated solid is filtered (cold) and rinsed with cold tetrahydrofuran. The filtrate is concentrated at reduced pressure to yield the corresponding succinimide ester.

Other imide esters of the products of Example 5 are prepared in like manner.

EXAMPLE 7

Radioiodinations of para-tri-n-butyltinbenzonitrile and the succinimide esters of para-tri-n-butyltinphenylpropionic acid and para-tri-n-butyltinhippuric acid.

A vial containing approximately 1 millicurie of sodium iodide-131 in 0.1M sodium hydroxide is diluted with phosphate buffer to pH approximately 7.5 and is evaporated to near dryness at 60° C. The vial is then cooled to 0° C., and a 10 microliter aliquot of a 2 milligram/milliliter solution of an aryltin product of either Example 2 or Example 6 in absolute methanol is added thereto. Immediately thereafter a 50 microliter aliquot of a 1 milligram/milliliter solution of N-chlorosuccinimide in absolute methanol is added. The reaction mixture is stirred for five minutes at 0° C., and then a 10 microliter aliquot of sodium thiosulfate solution is added to reduce any remaining volatile radiohalide.

The reaction product can be recovered from the reaction mixture by radio-HPLC. However, for better yield of radiolabel it is preferable to proceed directly to the conjugation step of Example 8.

EXAMPLE 8

Protein labeling with radiohalogenated small molecules.

The radiohalogenated succinimide esters of Example 7 are added directly to a buffered protein solution (pH approximately 8.5) immediately after the radiohalogenation reaction is complete.

The radiohalogenated cyano compound of Example 7 is converted to the corresponding imidate methyl ester before reaction with protein. The imidate ester is synthesized by adding 50 microliters of methanol saturated with anhydrous hydrochloric acid (gas) to the reaction mixture at 0° C. for 30 minutes. This solution is thereafter added directly to the buffered protein solution (>500 microliters) as above.

The radiohalogenated protein products of Example 8 can be used for radiodiagnosis and therapy. For example, monoclonal antibodies that are specifically reactive with tumor cell associated antigens can be radiohalogenated by this method and then used for imaging tumor cell location in the body of a mammal: for example, an effective amount of the radiohalogenated antibody can be introduced, e.g., by intravenous injection, into the body, and thereafter the body can be scanned with a scintillation detector such as a gamma camera. Such radiohalogenated antibodies can also be introduced into the body of a mammal for the purpose of tumor radiotherapy. As another example, radiohalogenated antibodies or fragments of antibodies of this invention can be employed in in vitro radioimmunoassays. All of the aforementioned radiohalogenated proteins are stably radiolabeled because the radiohalogen is substituted onto a nonactivated aromatic ring of the conjugate. Moreover, by thereby substituting the radiohalogen in the para or meta-position without the presence of a hydroxyl functionality, the radiohalogen is made less susceptible to catabolism by the body's deiodinase enzymes.

While the present invention has been described in conjunction with preferred embodiments, one of ordinary skill after reading the foregoing specification will be able to effect various changes, substitutions of equivalents, and other alterations to the compositions and methods set forth herein. It is therefore intended that the protection granted by Letters Patent hereon be limited only by the definition contained in the appended claims and equivalents thereof.

The embodiments of the invention in which an exclusive property or privilege is claimed are defined as follows:

1. A composition comprising a nonradioactive compound of the formula X-Ar*-R and a compound having the formula:

*X-Ar-R wherein

Ar is an aromatic ring;

R is a chemical bond or a substituent containing 1 to 12 straight-chain carbon atoms that does not activate Ar to electrophilic substitution on the order produced by hydroxy or amino substitution of the ring, wherein said bond or said substituent has attached thereto a functional group suitable for covalent linkage to a protein under conditions that preserve the biological activity of the protein, said functional group selected from phenolic ester, imide ester, imidate ester, anhydride, acylsuccinimide, aldehyde, isothiocyanate, diazo, hydrazine, alkyl halide and maleimide;

*X is a radioisotope of iodine, bromine, fluorine or astatine and is para- or meta-positioned relative to substituent R and X is the non-radioactive form of *X; and wherein said composition has high specific activity.

2. A method of radiohalogenating a protein comprising the step of reacting said protein with at least one composition of claim 1.

3. A compound having the formula:

*X-Ar-R wherein

Ar is an aromatic ring;

R is a chemical bond or a substituent containing 1 to 12 straight-chain carbon atoms that does not activate Ar to electrophilic substitution on the order produced by hydroxy or amino substitution of the ring, wherein said bond or said substituent has attached thereto a functional group suitable for covalent linkage to a protein under conditions that preserve the biological activity of the protein, said functional group selected from phenolic ester, imide ester, imidate ester, anhydride, acylsuccinimide, aldehyde, isothiocyanate, diazo, hydrazine, alkyl halide and maleimide; and

*X is a radioisotope of iodine, bromine, fluorine or astatine and is para- or meta-positioned relative to substituent R.

4. The compound of claim 3 wherein *X is $^{123}I$, $^{125}I$, $^{131}I$, $^{75}Br$, $^{76}Br$, $^{18}F$ or $^{211}At$.

5. The compound of claim 3 wherein R is imide ester, alkyl imide ester, amido alkyl imide ester, imidate ester, alkyl imidate ester or amido alkyl imidate ester.

6. The compound of claim 3 selected from those of the group: N-succinimidyl 3(4'-[*X]halophenyl)proprionate; methyl 3-(4'-[*X]halophenyl)propioimidate; N-succinimidyl 4-[*X]halobenzoate; methyl 4-[*X]halobenzimidate; N-succinimidyl 4-[*X]halobenzamidoacetate; N-succinimidyl 4-[*X]halohippurate; methyl 4-[*X]halobenzamidoacetiimidate; and 4-[*X]halobenzamidoacetonitrile.

7. A method of radiohalogenating a protein comprising the step of reacting, in an aqueous medium, amino, thiol or hydroxy groups on said protein with at least one compound of claim 3.

* * * * *

UNITED STATES PATENT AND TRADEMARK OFFICE

CERTIFICATE OF CORRECTION

PATENT NO. : 5,045,303
DATED : September 3, 1991
INVENTOR(S) : Wilbur et al.

It is certified that error appears in the above-indentified patent and that said Letters Patent is hereby corrected as shown below:

In Column 10, line 25 [claim 1], please change "X-Ar*-R" to --X-Ar-R--.

In Column 11, line 7 [claim 4], after "$^{76}$Br," please insert --$^{77}$Br,--.

Signed and Sealed this

Sixteenth Day of January, 1996

Attest:

BRUCE LEHMAN

Attesting Officer

Commissioner of Patents and Trademarks